(12) United States Patent
Wang et al.

(10) Patent No.: US 10,300,243 B2
(45) Date of Patent: May 28, 2019

(54) CATHETER APPARATUS AND OPERATING METHOD THEREOF

(71) Applicant: Crystalvue medical corporation, Taoyuan (TW)

(72) Inventors: William Wang, Taoyuan (TW); Meng-Shin Yen, Taipei (TW); Chung-Cheng Chou, Taoyuan (TW); Chung-Ping Chuang, Taoyuan (TW)

(73) Assignee: CRYSTALVUE MEDICAL CORPORATION, Taoyuan (TW)

( * ) Notice: Subject to any disclaimer, the term of this patent is extended or adjusted under 35 U.S.C. 154(b) by 343 days.

(21) Appl. No.: 15/286,647

(22) Filed: Oct. 6, 2016

(65) Prior Publication Data

US 2017/0100562 A1    Apr. 13, 2017

Related U.S. Application Data

(60) Provisional application No. 62/238,195, filed on Oct. 7, 2015.

(51) Int. Cl.
*A61M 25/10* (2013.01)
*A61M 25/00* (2006.01)
*A61M 25/01* (2006.01)

(52) U.S. Cl.
CPC .. *A61M 25/0017* (2013.01); *A61M 25/10184* (2013.11); *A61M 2025/0166* (2013.01)

(58) Field of Classification Search
CPC ........ A61M 25/0017; A61M 25/10184; A61M 2025/0166
See application file for complete search history.

(56) References Cited

U.S. PATENT DOCUMENTS

| | | | |
|---|---|---|---|
| 2005/0192652 A1* | 9/2005 | Cioanta | A61F 7/12 607/105 |
| 2012/0259216 A1* | 10/2012 | Gerrans | A61B 1/00165 600/435 |
| 2014/0309550 A1* | 10/2014 | Iglesias | A61B 5/202 600/561 |

* cited by examiner

*Primary Examiner* — Kai H Weng
(74) *Attorney, Agent, or Firm* — McClure, Qualey & Rodack, LLP

(57) ABSTRACT

A catheter apparatus includes a replaceable module, a main body portion and a sensing module. The main body portion includes a tube, a urine guide opening and an elastic unit. The replaceable module includes a control unit. A first terminal of the tube is coupled to the replaceable module and a second terminal of the tube is inserted into the bladder. The urine guide opening is disposed at the second terminal of the tube and used to guide urine into the tube when the second terminal of the tube is inserted into the bladder. The elastic unit is disposed at the second terminal of the tube and coupled to the control unit. The sensing module is coupled to the control unit and used to sense whether the second terminal of the tube is inserted to the correct position in the bladder and transmit sensing result to the control unit.

6 Claims, 9 Drawing Sheets

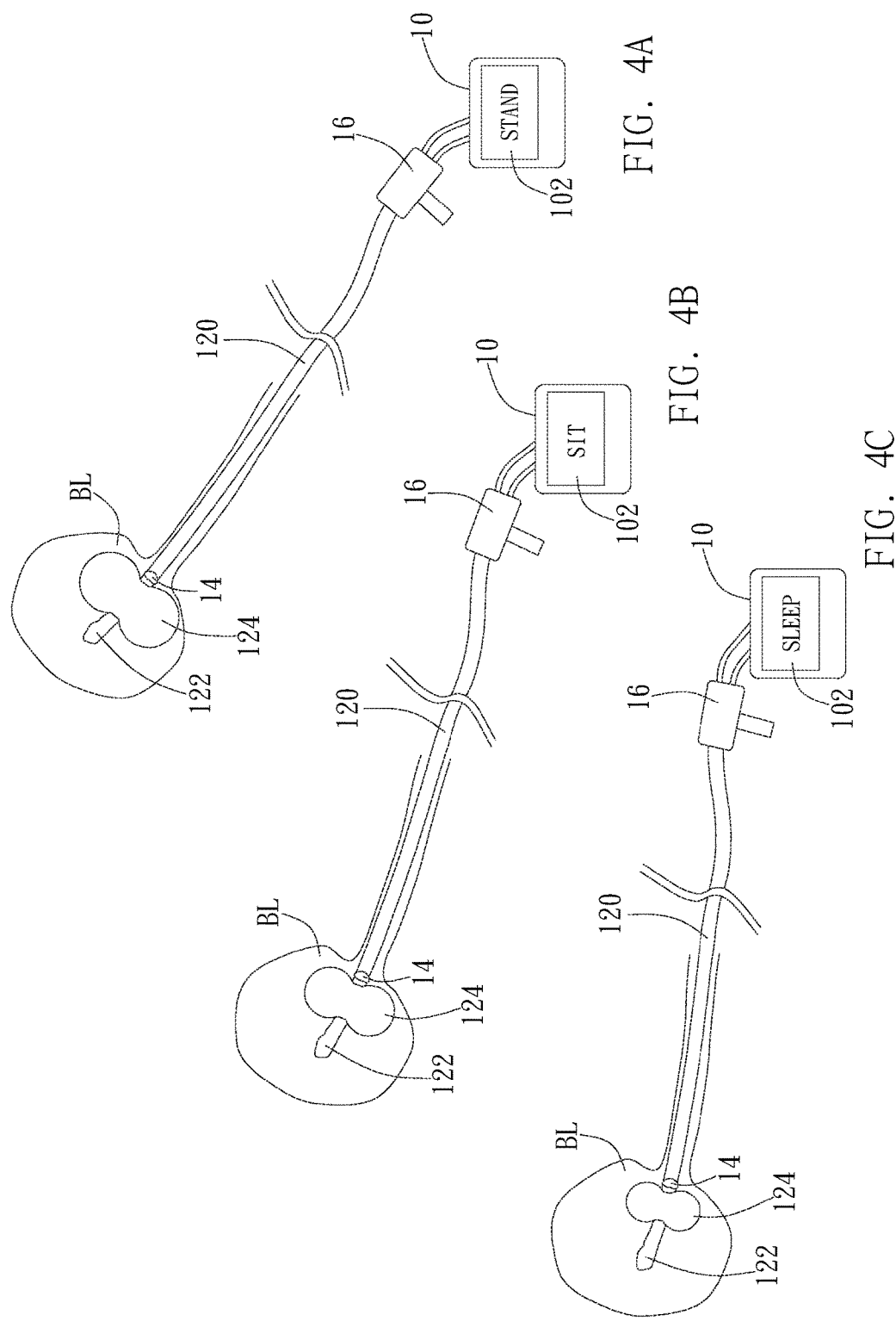

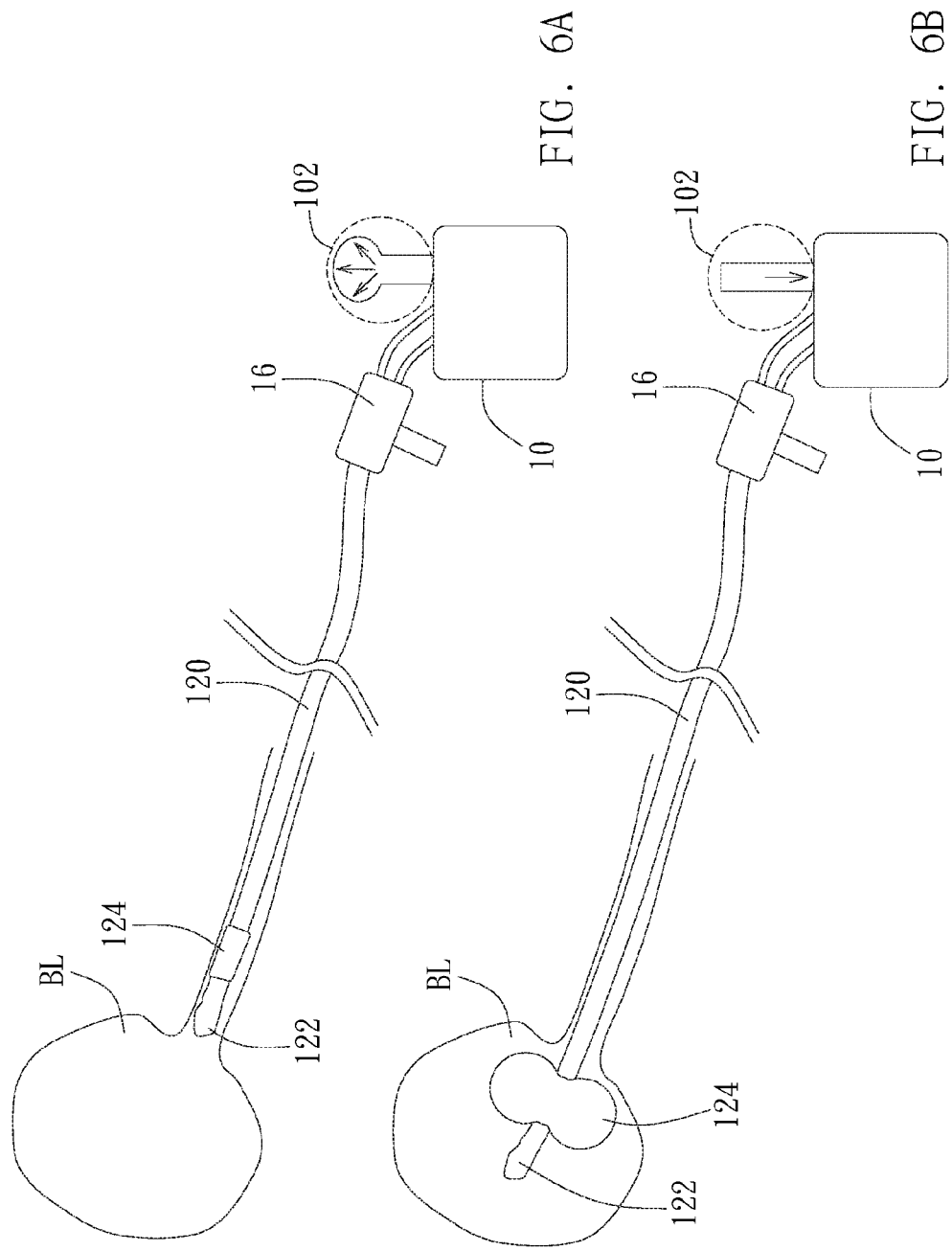

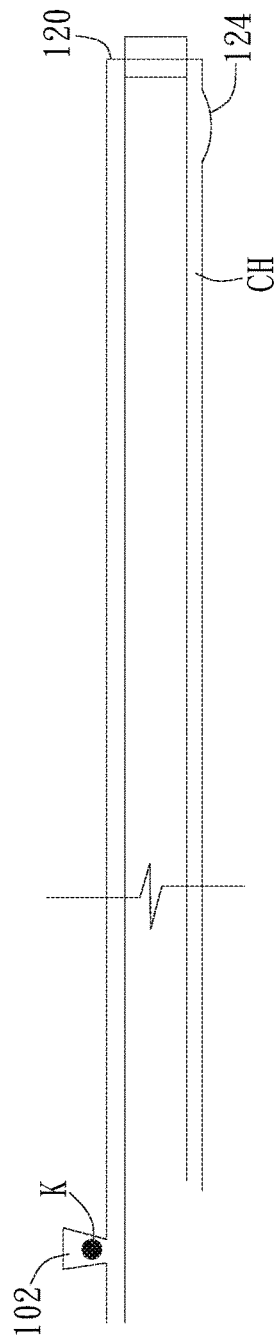
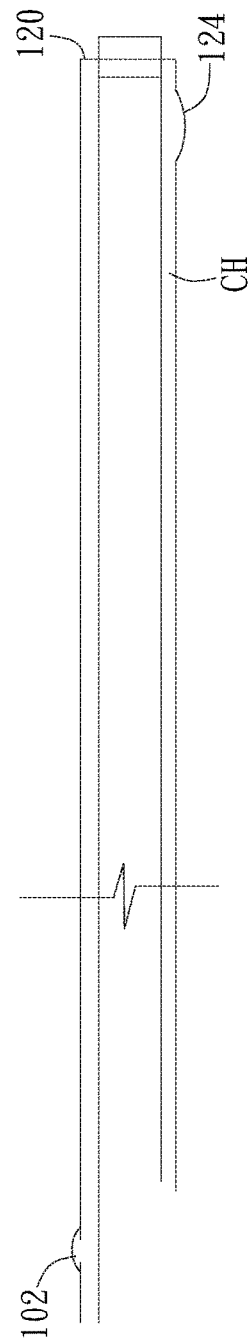
FIG. 7A
FIG. 7B

CATHETER APPARATUS AND OPERATING METHOD THEREOF

BACKGROUND OF THE INVENTION

1. Field of the Invention

This invention relates to a catheter apparatus, especially to a catheter apparatus and an operating method thereof 2. Description of the prior art In general, the catheter apparatus is used to discharge the urine from the bladder of the patient. Its operating theorem is to insert the sterile catheter into the bladder of the patient and the balloon is swelled and disposed in the bladder without departing from the bladder. And then, the operator will manually operate the aspirator pump, so that the urine in the bladder of the patient can be smoothly discharged to the urine collector out of the body of the patient to achieve the effects of keeping clear and dry, preventing wound infection or bladder decompression before and after surgery.

However, the current catheter apparatus still has many drawbacks in practical applications. For example, when the catheter apparatus is inserted into the bladder of the patient, the operator fails to immediately know whether the catheter apparatus is suitably inserted into the correct position in the bladder of the patient. Therefore, the operator may swell the balloon and start the aspirator pump too early when the catheter apparatus has not been inserted to the correct position of the bladder. This will make the patient uncomfortable and the urine discharging effect will be poor. In addition, when the conventional catheter apparatus is used to discharge urine from the bladder of the patient, the patient may have different postures such as the standing posture, the sitting posture or the lying posture, but the conventional catheter apparatus fails to correspondingly adjust the size of the swelled balloon in the bladder according to the different postures of the patient. Even the size of the swelled balloon in the bladder is fixed, the patient will still feel painful under some postures.

Therefore, the invention provides a catheter apparatus and an operating method thereof to overcome the problems occurred in the above-mentioned prior arts.

SUMMARY OF THE INVENTION

A preferred embodiment of the invention is a catheter apparatus. In this embodiment, the catheter apparatus is used for discharging a urine from a bladder. The catheter apparatus includes a replaceable module, a main body portion and a sensing module. The main body portion includes a tube, a urine guide opening and an elastic unit. The replaceable module includes a control unit. A first terminal of the tube is coupled to the replaceable module and a second terminal of the tube is inserted into the bladder. The urine guide opening is disposed at the second terminal of the tube and used to guide urine into the tube when the second terminal of the tube is inserted into the bladder. The elastic unit is disposed at the second terminal of the tube and coupled to the control unit. The sensing module is coupled to the control unit and used to sense whether the second terminal of the tube is inserted to the correct position in the bladder and transmit the sensing result to the control unit.

In an embodiment, if the sensing result is that the second terminal of the tube is inserted to the correct position in the bladder, the control unit automatically controls the elastic unit to swell in the bladder, so that the elastic unit can be disposed in the bladder without departing from the bladder.

In an embodiment, the replaceable module further includes an indicating unit, coupled to the control unit, for indicating the sensing result. the indicating unit is a display monitor, a speaker, a light emitting unit, a hollow tube including an indicator or an inflatable elastomer used to indicate the sensing result by displaying a text, a symbol or an image, making a sound, emitting a light, the high position or low position of the indicator in the hollow tube or whether the elastomer is inflated.

In an embodiment, the elastic unit and the indicating unit are disposed in the same air flow passage and an air flows through the elastic unit at first, when the second terminal of the tube is not inserted into the correct position in the bladder, the elastic unit fails to swell and the air flowing through the elastic unit flows to the indicating unit to move the indicator of the indicating unit from a first position to a second position; when the second terminal of the tube is inserted into the correct position in the bladder, the elastic unit can swell and the air flowing through the elastic unit flows into the elastic unit instead of flowing to the indicating unit to move the indicator of the indicating unit to the first position.

In an embodiment, the replaceable module further includes a mode selecting unit, coupled to the control unit and used by a user to select a using mode, and the control unit correspondingly adjusts a size of the swelled elastic unit in the bladder according to the using mode.

In an embodiment, the elastic unit and the indicating unit are disposed in the same air flow passage and an air flows through the elastic unit at first, when the second terminal of the tube is not inserted into the correct position in the bladder, the elastic unit fails to swell and the air flowing through the elastic unit flows to the indicating unit to move the indicator of the indicating unit from a first position to a second position; when the second terminal of the tube is inserted into the correct position in the bladder, the elastic unit can swell and the air flowing through the elastic unit flows into the elastic unit instead of flowing to the indicating unit to move the indicator of the indicating unit to the first position.

In an embodiment, the replaceable module further includes a mode selecting unit, coupled to the control unit and used by a user to select a using mode, and the control unit correspondingly adjusts a size of the swelled elastic unit in the bladder according to the using mode.

Another embodiment of the invention is a catheter apparatus operating method. In this embodiment, the catheter apparatus operating method is used for operating a catheter apparatus to discharge a urine from a bladder. The catheter apparatus includes a replaceable module, a main body portion and a sensing module. The replaceable module includes a control unit, the main body portion including a tube, a urine guide opening and an elastic unit. The catheter apparatus operating method includes steps of: (a) coupling a first terminal of the tube to the replaceable module and inserting a second terminal of the tube into the bladder; (b) disposing the urine guide opening and the elastic unit at the second terminal and the first terminal of the tube respectively; and (c) using the sensing module to sense whether the second terminal of the tube is inserted to a correct position in the bladder and transmitting a sensing result to the control unit.

Compared to the prior art, the catheter apparatus and operating method thereof have the following advantages of:

(1) When the catheter apparatus is operated in the manual mode, the operator can immediately know whether the catheter is inserted to the correct position in the bladder of the patient according to the sensing result of the sensing unit indicated by the indicating unit; therefore, the operator can properly operate the catheter apparatus to reduce the discomfort of the patient.

(2) When the catheter apparatus is operated in the automatic mode, the catheter apparatus can automatically perform the procedures of swelling the balloon in the bladder of the patient and starting the pump directly according to the sensing result of the sensing unit; therefore, the burden of the operator can be largely reduced.

(3) The catheter apparatus can correspondingly adjust the size of the swelled balloon in the bladder of the patient according to different modes; therefore, the catheter apparatus can be adjusted with different postures of the patient and the patient can be more comfortable during catheterization.

The advantage and spirit of the invention may be understood by the following detailed descriptions together with the appended drawings.

BRIEF DESCRIPTION OF THE APPENDED DRAWINGS

FIG. 4A~FIG. 4C illustrate schematic diagrams of the different sizes of the swelled elastic unit in the bladder when the catheter apparatus is operated in the standing posture mode, the sitting posture mode or the lying posture mode respectively.

Figure 5A:
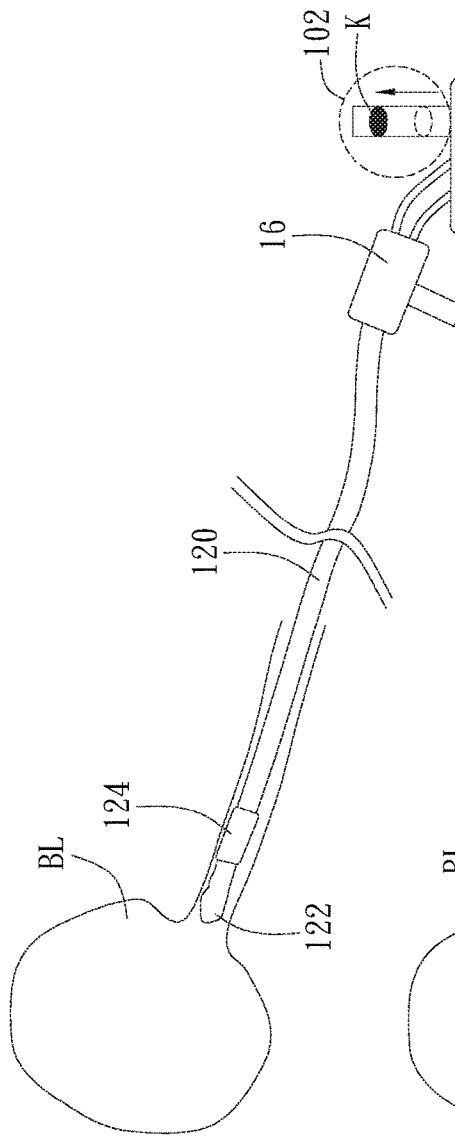
Figure 5B:
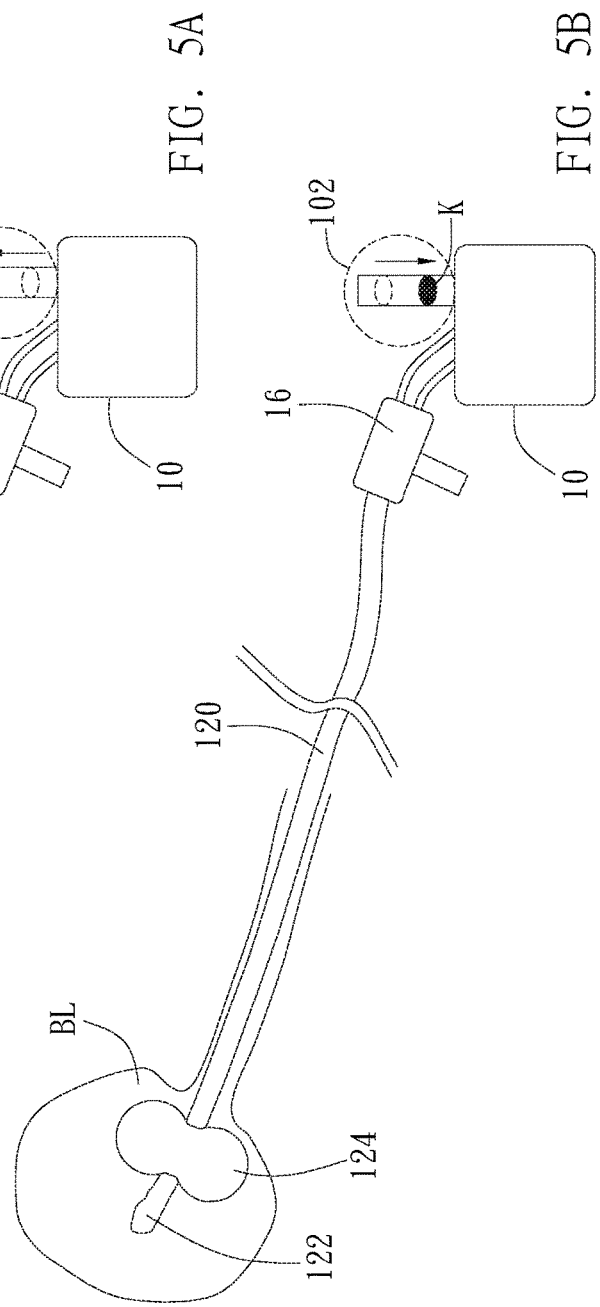

FIG. 5A~FIG. 5B illustrate schematic diagrams of the indicating unit indicating the sensing result through the high position or low position of the indicator in the hollow tube.

FIG. 6A~FIG. 6B illustrate schematic diagrams of the indicating unit indicating the sensing result through the elastomer is inflated or not.

FIG. 7A~FIG. 7B illustrate different embodiments of disposing the elastic unit and the indicating unit at the second terminal and the first terminal of the tube respectively and in the same air flow passage.

Figure 8A:
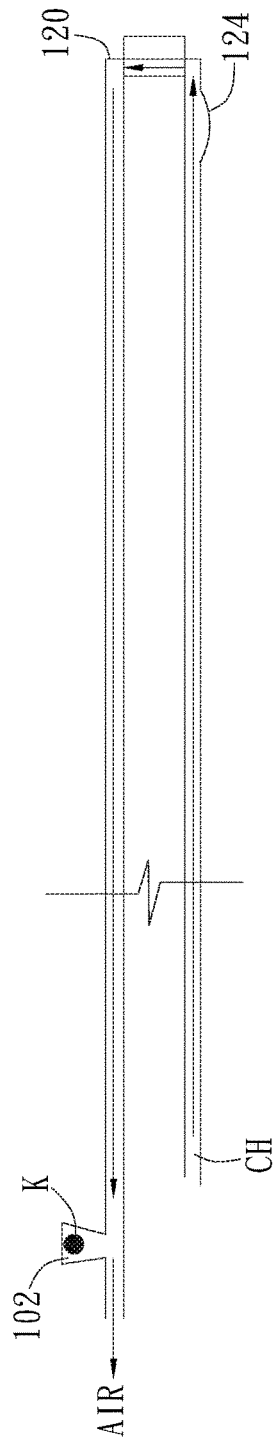

FIG. 8A illustrates a schematic diagram of the elastic unit failing to swell when the second terminal of the tube not inserting into the bladder yet and the air can flow to the indicating unit to lift the indicator of the indicating unit from the lower first position to the higher second position.

Figure 8B:
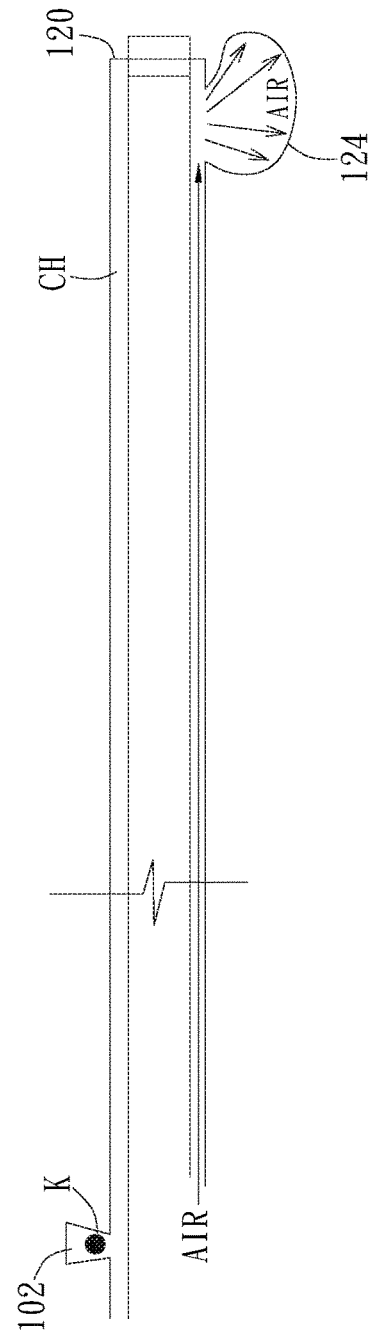

FIG. 8B illustrates a schematic diagram of the elastic unit can swell when the second terminal of the tube inserting into the bladder and most of the air flowing into the elastic unit to swell the elastic unit instead of flowing to the indicating unit and the indicator of the indicating unit declining back to the lower first position.

Figure 9:
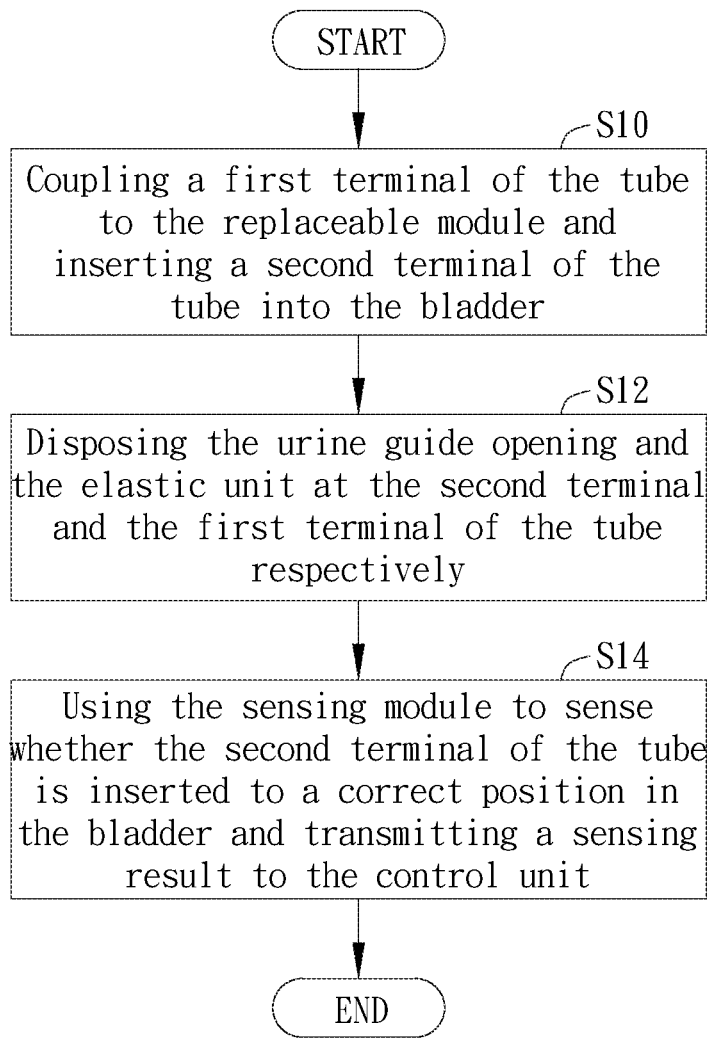

FIG. 9 illustrates a flowchart of the catheter apparatus operating method in another embodiment of the invention.

DETAILED DESCRIPTION OF THE INVENTION

An embodiment of the invention is a catheter apparatus. In this embodiment, the catheter apparatus is used to insert into the bladder to discharge urine from the bladder.

Figure 1:
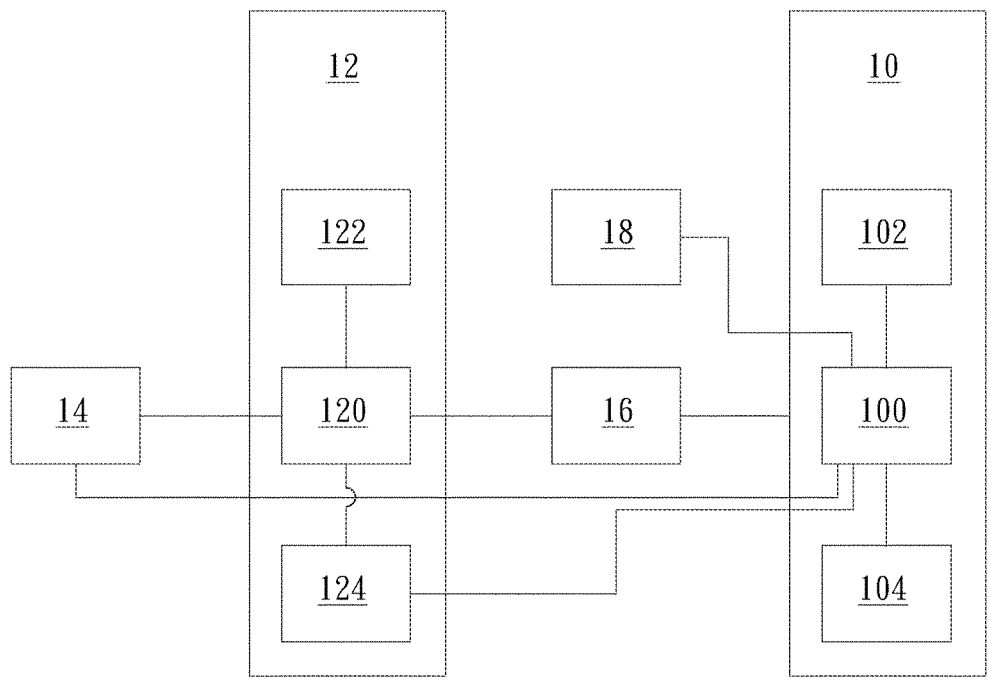
FIG. 1 illustrates a functional block diagram of the catheter apparatus in a preferred embodiment of the invention.

Please refer to FIG. 1. FIG. 1 illustrates a functional block diagram of the catheter apparatus in this embodiment. As shown in FIG. 1, the catheter apparatus 1 can include a replaceable module 10, a main body portion 12, a sensing module 14, a urine discharging module 16 and a position detecting module 18. Wherein, the replaceable module 10 can include a control unit 100, an indicating unit 102 and a mode selecting unit 104; the main body portion 12 can includes a tube 120, a urine guide opening 122 and an elastic unit 124. The control unit 100 is coupled to the indicating unit 102, the mode selecting unit 104, the elastic unit 124, the sensing module 14 and the position detecting module 18 respectively; the tube 120 is coupled to the urine guide opening 122, the elastic unit 124, the urine discharging module 16 and the sensing module 14 respectively; the urine discharging module 16 is coupled to the replaceable module 10 and the tube 120 respectively.

In this embodiment, the tube 120 is a hollow tube having a first terminal and a second terminal, wherein the first terminal of the tube 120 is coupled to the replaceable module 10 and the second terminal of the tube 120 is used to insert into the bladder. The elastic unit 124 is disposed at the second terminal of the tube 120 and coupled to the control unit 100. In fact, the elastic unit 124 can be an inflatable elastomer, such as a balloon, but not limited to this.

The sensing module 14 is used to sense whether the second terminal of the tube 120 is inserted to the correct position in the bladder and transmit the sensing result to the control unit 100. In fact, the sensing module 14 can sense through an optical method, an electronic method or mechanical method to obtain the sensing result, but not limited to this.

The position detecting module 18 is used to detect the position of the patient and transmit the detecting result to the control unit 100, and then the control unit 100 will determine the posture of the patient according to the detecting result and further adjust the operating mode of the catheter apparatus 1. In fact, the position detecting module 18 can be worn on the body of the patient with a wearing device and the position detecting module 18 can transmit the detecting result to the control unit 100 through wireless transmitting method or wired transmitting method, but not limited to this.

Figure 2:
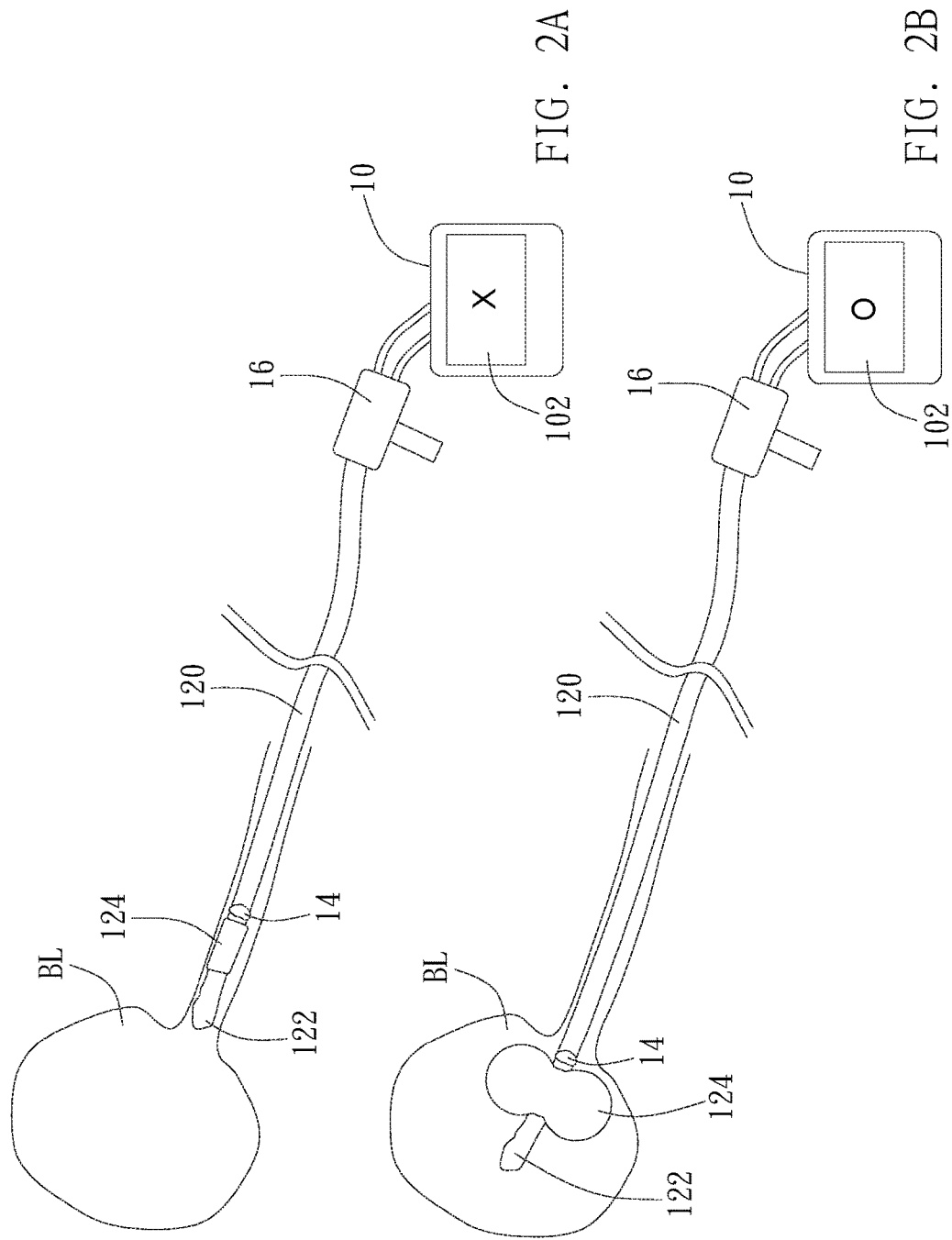
FIG. 2A illustrates a schematic diagram of the second terminal of the tube not inserting to the correct position in the bladder yet.
FIG. 2B illustrates a schematic diagram of the second terminal of the tube inserting to the correct position in the bladder.

Please refer to FIG. 2A and FIG. 2B. FIG. 2A illustrates a schematic diagram of the second terminal of the tube 120 not inserting to the correct position in the bladder BL yet; FIG. 2B illustrates a schematic diagram of the second terminal of the tube 120 inserting to the correct position in the bladder BL.

If the sensing result the control unit 100 receives from the sensing module 14 is that the second terminal of the tube 120 has not inserted to the correct position in the bladder BL yet, the elastic unit 124 will not swell, as shown in FIG. 2A; if the sensing result the control unit 100 receives from the sensing module 14 is that the second terminal of the tube 120 has already inserted to the correct position in the bladder BL, the control unit 100 will automatically control the elastic unit 124 to swell in the bladder BL, so that the swelled elastic unit 124 can be disposed in the bladder BL without departing from the bladder BL.

Figure 3:
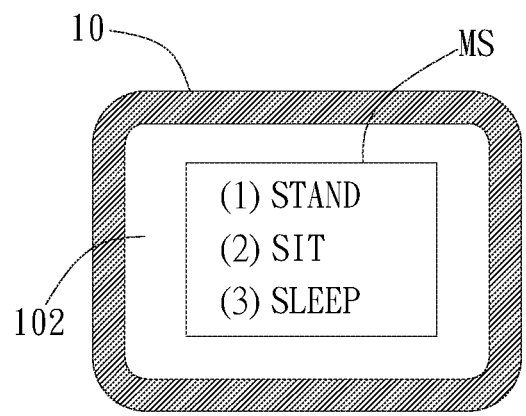
FIG. 3 illustrates a schematic diagram of the mode menu displayed by the mode selecting unit disposed on the replaceable module.

In this embodiment, the mode selecting unit 104 of the replaceable module 10 is used by the user to select a using mode. For example, as shown in FIG. 3, the mode selecting unit 104 can be a touch monitor disposed on the replaceable module 10 used to display a mode menu MS; therefore, the user can touch the touch monitor to select the standing posture mode (STAND), the sitting posture mode (SIT) or the lying posture mode (SLEEP) from the mode menu MS.

In addition, the mode menu MS can include options such as the automatic mode and the manual mode. When the user selects the automatic mode through the mode selecting unit 104, the catheter apparatus 1 will be operated in the automatic mode; when the user switches to the manual mode through the mode selecting unit 104, the catheter apparatus 1 will be changed to be controlled by the user. Therefore, the automatic mode and the manual mode can be switched based on practical needs of the user.

When the catheter apparatus 1 is used to discharge urine from the bladder of the patient, the patient can have different postures such as the standing posture, the sitting posture or the lying posture; therefore, when the catheter apparatus 1 is operated in the manual mode, the control unit 100 of the invention will correspondingly adjust the size of the swelled elastic unit 124 in the bladder according to the different modes (namely the different postures of the patient) selected by the patient through the mode selecting unit 104 to avoid pain and discomfort to the patient; when the catheter apparatus 1 is operated in the automatic mode, the control unit 100 of the invention can automatically determine the posture of the patient (e.g., the standing posture, the sitting posture or the lying posture) according to the detecting result of the patient's position detected by the position detecting module 18, and then the control unit 100 can corresponding change the operating mode of the catheter apparatus 1 (e.g., the standing posture mode, the sitting posture mode or the lying posture mode) to adjust the size of the swelled elastic unit 124 in the bladder to avoid pain and discomfort to the patient.

For example, FIG. 4A~FIG. 4C illustrate schematic diagrams of the different sizes of the swelled elastic unit in the bladder when the catheter apparatus is operated in the standing posture mode (STAND), the sitting posture mode (SIT) or the lying posture mode (SLEEP) respectively. As shown in FIG. 4A~FIG. 4C, it can be found that when the posture of the patient is the standing posture, the size of the swelled elastic unit 124 in the bladder BL will become largest; when the posture of the patient is the lying posture, the size of the swelled elastic unit 124 in the bladder BL will become smallest; when the posture of the patient is the sitting posture, the size of the swelled elastic unit 124 in the bladder BL will become middle.

When the elastic unit 124 is swelled in the bladder BL and the second terminal of the tube 120 is fixed in the bladder BL, the urine guide opening 122 disposed at the second terminal of the tube 120 can start to guide the urine from the bladder BL to the tube 120, so that the urine can be discharged out of the bladder BL through the tube 120.

When the urine flows from the second terminal of the tube 120 to the first terminal of the tube 120, the urine discharging module 16 disposed at the first terminal of the tube 120 can start to discharge the urine out of the tube 120. In fact, the urine discharging module 16 can have a function of pump to help the discharging of the urine from the bladder BL to a urine collector, but not limited to this. In addition, the urine discharging module 16 can also have a function of urine analysis to analyze the urine before the urine is discharged to the urine collector, so that it can determine whether the data and indexes of the urine are normal according to the analyzing result.

In this embodiment, the indicating unit 102 of the replaceable module 10 is used to indicate the sensing result to let the user know the sensing result. In fact, the form of the indicating unit 102 has no limitations. The indicating unit 102 can be a display monitor, a speaker, a light emitting unit, a hollow tube including an indicator or an inflatable elastomer used to indicate the sensing result by displaying a text, a symbol or an image, making a sound, emitting a light, the high position or low position of the indicator in the hollow tube or whether the elastomer is inflated.

For example, it is assumed that the indicating unit 102 is the display monitor indicating the sensing result by displaying a symbol. When the indicating unit 102 displays "X", it represents that the second terminal of the tube 120 has not inserted to the correct position in the bladder BL yet, as shown in FIG. 2A; when the indicating unit 102 displays "O", it represents that the second terminal of the tube 120 has been inserted to the correct position in the bladder BL, as shown in FIG. 2B.

It should be noticed that the indicating unit 102 and the mode selecting unit 104 of the replaceable module 10 can be integrated together in some embodiments. For example, if the indicating unit 102 displays text, symbol and image to indicate the sensing result and the mode selecting unit 104 displays the mode menu for the user to select a using mode, then the indicating unit 102 and the mode selecting unit 104 can be integrated in the same touch monitor disposed on the replaceable module 10 to reduce the volume.

In another embodiment, it is assumed that the indicating unit 102 is a transparent hollow tube including an indicator K using the high position or low position of the indicator K in the hollow tube to indicate the sensing result. When the indicator K of the indicating unit 102 is located in a higher second position, it represents that the second terminal of the tube 120 has not inserted to the correct position in the bladder BL yet, as shown in FIG. 5A; when the indicator K of the indicating unit 102 is located in a lower first position, it represents that the second terminal of the tube 120 has been inserted to the correct position in the bladder BL, as shown in FIG. 5B.

In another embodiment, it is assumed that the indicating unit 102 is an inflatable elastomer indicating the sensing result by whether the elastomer is inflated by air flow. When the elastomer is inflated by air flow, it represents that the second terminal of the tube 120 has not inserted to the correct position in the bladder BL yet, as shown in FIG. 6A; when the elastomer is not inflated by air flow, it represents that the second terminal of the tube 120 has been inserted to the correct position in the bladder BL, as shown in FIG. 6B.

In another embodiment, it is assumed that the indicating unit 102 is a speaker making a sound to indicate the sensing result. The indicating unit 102 can make the sound of music to represent that the second terminal of the tube 120 has been inserted to the correct position in the bladder BL and the indicating unit 102 can make rapid warning sound to represent that the second terminal of the tube 120 has not inserted to the correct position in the bladder BL yet.

In another embodiment, it is assumed that the indicating unit 102 is a light emitting unit emitting a light to indicate the sensing result. The indicating unit 102 can emit a green light to represent that the second terminal of the tube 120 has been inserted to the correct position in the bladder BL and the indicating unit 102 can emit a red light to represent that the second terminal of the tube 120 has not inserted to the correct position in the bladder BL yet.

Then, please refer to FIG. 7A and FIG. 7B. As shown in FIG. 7A and FIG. 7B, the elastic unit 124 and the indicating unit 102 are disposed at the second terminal and the first terminal of the tube 120 respectively and the elastic unit 124 and the indicating unit 102 are both in the same air flow passage CH. It should be noticed that, in an embodiment, the indicating unit 102 of FIG. 7A is a hollow tube including an indicator K and the elastic unit 124 is an inflatable elastomer; in another embodiment, the elastic unit 124 and the indicating unit 102 of FIG. 7B are both inflatable elastomers.

Taking FIG. 7A for example, it is assumed that the air flow AIR in the air flow passage CH will flow through the elastic unit 124. When the second terminal of the tube 120 has not inserted to the correct position in the bladder BL yet, the elastic unit 124 fails to swell and the air flow AIR flowing through the elastic unit 124 will continuously flow to the indicating unit 102 to move the indicator K of the indicating unit 102 from a lower first position to a higher second position, as shown in FIG. 8A; when the second terminal of the tube 120 is inserted into the correct position in the bladder BL, the elastic unit 124 can swell and most of the air flow AIR flowing through the elastic unit 124 will flow into the elastic unit 124 instead of flowing to the indicating unit 102 to move the indicator K of the elastic unit 124 back to the lower first position, as shown in FIG. 8B. By doing so, the user only needs to observe that the indicator K of the indicating unit 102 is located at the lower first position or the higher second position to know whether the second terminal of the tube 120 is inserted into the correct position in the bladder BL to start to perform the urine discharging procedure.

Another embodiment of the invention is a catheter apparatus operating method. In this embodiment, the catheter apparatus operating method is used for operating a catheter apparatus to discharge a urine from a bladder. The catheter apparatus includes a replaceable module, a main body portion and a sensing module. The replaceable module includes a control unit, the main body portion including a tube, a urine guide opening and an elastic unit, but not limited to this.

Please refer to FIG. 9. FIG. 9 illustrates a flowchart of the catheter apparatus operating method in this embodiment. As shown in FIG. 9, the catheter apparatus operating method includes the following steps of:

Step S10: coupling a first terminal of the tube to the replaceable module and inserting a second terminal of the tube into the bladder;

Step S12: disposing the urine guide opening and the elastic unit at the second terminal and the first terminal of the tube respectively; and Step S14: using the sensing module to sense whether the second terminal of the tube is inserted to a correct position in the bladder and transmitting a sensing result to the control unit.

In practical applications, the sensing module can use an optical method, an electronic method or a mechanical method to perform the step S14 to sense, but not limited to this. In addition, the control unit can be switched to operate in the manual mode.

It should be noticed that if the sensing result of the sensing module is that the second terminal of the tube has been inserted into the correct position in the bladder, then the control unit will automatically control the elastic unit to swell in the bladder, so that the swelled elastic unit can be disposed in the bladder without departing from the bladder. In addition, the replaceable module can further include a mode selecting unit used by the user to select a using mode and then the control unit correspondingly adjusts a size of the swelled elastic unit in the bladder according to the using mode, but not limited to this.

In an embodiment, the replaceable module can further include an indicating unit. The indicating unit is coupled to the control unit and used to indicate the sensing result. In fact, the indicating unit can indicate the sensing result through different ways, such as making a sound or emitting a light, but not limited to this.

Compared to the prior art, the catheter apparatus and operating method thereof have the following advantages of:

(1) When the catheter apparatus is operated in the manual mode, the operator can immediately know whether the catheter is inserted to the correct position in the bladder of the patient according to the sensing result of the sensing unit indicated by the indicating unit; therefore, the operator can properly operate the catheter apparatus to reduce the discomfort of the patient.

(2) When the catheter apparatus is operated in the automatic mode, the catheter apparatus can automatically perform the procedures of swelling the balloon in the bladder of the patient and starting the pump directly according to the sensing result of the sensing unit; therefore, the burden of the operator can be largely reduced.

(3) The catheter apparatus can correspondingly adjust the size of the swelled balloon in the bladder of the patient according to different modes; therefore, the catheter apparatus can be adjusted with different postures of the patient and the patient can be more comfortable during catheterization.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A catheter apparatus for discharging urine from a bladder, the catheter apparatus comprising:
   a replaceable module comprising a control unit;
   a main body portion comprising:
      a tube having a first terminal and a second terminal, wherein the first terminal of the tube is coupled to the replaceable module and the second terminal of the tube is configured to be inserted into the bladder;
      a urine guide opening disposed at the second terminal of the tube and configured to guide the urine into the tube when the second terminal of the tube is inserted into the bladder; and
      an elastic unit disposed at the second terminal of the tube and coupled to the control unit; and
   a sensing module coupled to the control unit and configured to sense whether the second terminal of the tube is inserted to a correct position in the bladder and transmit a sensing result to the control unit;
   wherein the replaceable module further comprises:
   an indicating unit, coupled to the control unit and configured to indicate the sensing result;
   wherein the indicating unit is a display monitor, a speaker, a light emitting unit, a hollow tube comprising an indicator or an inflatable elastomer configured to indicate the sensing result by displaying a text, a symbol or an image, making a sound, emitting a light, a high position or a low position of the indicator in or whether the elastomer is inflated; the elastic unit is disposed in an air flow passage and the indicating unit is also disposed in the air flow passage, and air flows through the elastic unit at first, when the second terminal of the tube is not inserted into the correct position in the bladder, the elastic unit fails to swell and the air flowing through the elastic unit flows to the indicating unit to move the indicator of the indicating unit from a first position to a second position; when the second terminal of the tube is inserted into the correct position in the bladder, the elastic unit and the air flowing through the elastic unit flows into the elastic unit instead of flowing to the indicating unit to move the indicator of the indicating unit to the first position.

2. The catheter apparatus of claim 1, wherein if the sensing result is that the second terminal of the tube is inserted to the correct position in the bladder, the control unit automatically controls the elastic unit to swell in the bladder, so that the elastic unit is configured to be disposed in the bladder without departing from the bladder.

3. The catheter apparatus of claim 1, wherein the replaceable module further comprises:
a mode selecting unit, coupled to the control unit and usable by a user to select a using mode, and the control unit is configured to correspondingly adjusts a size of the elastic unit in the bladder according to the using mode.

4. A catheter apparatus operating method for operating a catheter apparatus to discharge a urine from a bladder, the catheter apparatus comprising a replaceable module, a main body portion and a sensing module, the replaceable module comprising a control unit, the main body portion comprising a tube, a urine guide opening and an elastic unit, the catheter apparatus operating method comprising steps of:
(a) coupling a first terminal of the tube to the replaceable module and inserting a second terminal of the tube into the bladder;
(b) disposing the urine guide opening and the elastic unit at the second terminal and the first terminal of the tube respectively; and
(c) using the sensing module to sense whether the second terminal of the tube is inserted to a correct position in the bladder and transmitting a sensing result to the control unit;

wherein the replaceable module further comprises an indicating unit coupled to the control unit and used to indicate the sensing result, the indicating unit is a display monitor, a speaker, a light emitting unit, a hollow tube comprising an indicator or an inflatable elastomer used to indicate the sensing result by displaying a text, a symbol or an image, making a sound, emitting a light, a high position or a low position of the indicator in the tube or whether the elastomer is inflated; the elastic unit is disposed in an air flow passage and the indicating unit is also disposed in the air flow passage, and air flows through the elastic unit at first, when the second terminal of the tube is not inserted into the correct position in the bladder, the elastic unit fails to swell and the air flowing through the elastic unit flows to the indicating unit to move the indicator of the indicating unit from a first position to a second position; when the second terminal of the tube is inserted into the correct position in the bladder, the elastic unit swells and the air flowing through the elastic unit flows into the elastic unit instead of flowing to the indicating unit to move the indicator of the indicating unit to the first position.

5. The catheter apparatus operating method of claim 4, wherein if the sensing result is that the second terminal of the tube is inserted to the correct position in the bladder, the control unit automatically controls the elastic unit to swell in the bladder, so that the elastic unit is disposed in the bladder without departing from the bladder.

6. The catheter apparatus operating method of claim 4, wherein the replaceable module further comprises a mode selecting unit used by a user to select a using mode, and the control unit correspondingly adjusts a size of the swelled elastic unit in the bladder according to the using mode.

* * * * *